United States Patent [19]

Marquez et al.

[11] Patent Number: 4,968,690
[45] Date of Patent: Nov. 6, 1990

[54] 3-DEAZANEPLANOCIN, INTERMEDIATES FOR IT, AND ANTIVIRAL COMPOSITION AND METHOD OF TREATMENT USING IT

[75] Inventors: Victor E. Marquez, Gaithersburg; John S. Driscoll, Rockville, both of Md.; Mu-Ill Lim, Trumbull, Conn.; Christopher K. Tseng, Silver Spring, Md.; Alberto Haces, Frederick, Md.; Robert I. Glazer, Gaithersburg, Md.

[73] Assignee: United States Government as represented by the Secretary of the Dept. of Health and Human Services, Washington, D.C.

[21] Appl. No.: 299,021

[22] Filed: Jan. 19, 1989

Related U.S. Application Data

[63] Continuation of Ser. No. 867,583, May 27, 1986, abandoned.

[51] Int. Cl.$^5$ .................... A61K 31/52; C07D 471/04
[52] U.S. Cl. .................... 514/303; 546/118; 546/296; 546/297; 546/301; 514/258; 514/261; 514/262; 514/267; 514/241; 514/245; 514/274; 544/220; 544/223; 544/254; 544/251; 544/264; 544/276; 544/277; 544/314; 544/317; 544/318; 549/437; 549/438
[58] Field of Search .................... 546/118; 514/303

[56] References Cited

U.S. PATENT DOCUMENTS

| | | | |
|---|---|---|---|
| 3,632,763 | 1/1972 | Hess et al. | 514/254 X |
| 4,386,093 | 5/1983 | Chiang et al. | 514/303 |
| 4,423,218 | 12/1983 | Otani et al. | 544/277 |
| 4,613,666 | 9/1986 | Fukukawa et al. | 544/277 |

FOREIGN PATENT DOCUMENTS 0219284  12/1984  Japan .................... 514/303

OTHER PUBLICATIONS

Montgomery, et al., Chemical Abstracts, vol. 96:192972v (1982).
DeClercq, et al., Chemical Abstracts, vol. 99:218w (1983).
Glazer, et al., Biochem. Biophys. Res. Commun. 1986. 135(2), pp. 688–694, Chemical Abstracts, vol. 104:199696a supplied U.S. Dept HHS, Chemical Abstracts, vol. 106:5380r (1987).

Primary Examiner—Diana G. Rivers
Attorney, Agent, or Firm—Robert Benson

[57] ABSTRACT

The new compound 3-deazaneplanocin A has been discovered to have potent anti-viral, anti-tumor activity and differentiating activity. A simple method for preparing 3-deazaneplanocin A has been developed involving nucleophilic substitution, which method can also be used to prepare a great variety of carbocyclic nucleosides.

4 Claims, 3 Drawing Sheets

4,968,690

3-DEAZANEPLANOCIN, INTERMEDIATES FOR IT, AND ANTIVIRAL COMPOSITION AND METHOD OF TREATMENT USING IT

The application is a continuation of application Ser. No. 867,583 filed May 27, 1986 now abandoned.

FIELD OF THE INVENTION

The present invention relates to antiviral and cancer chemotherapy and, more particularly, to the compound 3-deazaneplanocin A and related compounds and a method of preparation thereof, as well as the methods of preparation of a great variety of unsaturated (cyclopentenyl) carbocyclic nucleosides.

BACKGROUND OF THE INVENTION

Cancer can be considered to be a group of diseases that can occur in any tissue, organ, or system of the body. The causes of all cancers are not yet known, nor are there any reported major qualitative metabolic differences between cancer cells and host tissue cells of origin. Accordingly, cancer chemotherapy, unlike the chemotherapy of infectious diseases wherein the disease-causing organism itself offers a distinct metabolic or structural biological target, has far more restrictive fundamental concepts on which to pattern therapeutic treatment.

Most known classes of anticancer drugs exert their action principally because of quantitative differences in metabolic rates of production or levels of certain nucleic acids, enzymes, proteins, hormones, metabolic intermediates, etc., rather than because of qualitative biologic differences between cancer cells and normal cells. Thus, anticancer drugs do not exhibit selective toxicity in the classical sense.

Nucleosides, as a specific group of anticancer or antiviral agents, can be taken up selectively into cells via several mechanisms. Once the corresponding nucleotide is formed intracellularly, the nucleotide is then available for conversion into diphosphates, triphosphates, etc., and thereby can exert its cytotoxic effect via a number of possible mechanisms including effects on DNA polymerase, ribonucleoside diphosphate reductase, incorporation into DNA, and inhibition of DNA and cellular metabolism in general.

A number of anticancer nucleosides or bases have been described in the prior art. For example, cytosine arabinoside (ara-C), 5-fluorouracil, 5-fluorodeoxyuridine, 6-mercaptopurine, and thioguanine are among drugs currently used in the clinical treatment of cancer in human patients. Literally scores of pyrimidines, purines, structurally related heterocyclic bases, nucleosides, etc., have been synthesized and demonstrated to possess high cytotoxic activity in cell culture and, in a number of instances, in tumor-bearing animals. However, unfavorable therapeutic indexes have restricted the clinical use of this class of antimetabolites to the relatively few antineoplastic drugs presently used for the chemotherapy of cancer.

Recently, a number of compounds have been reported wherein the oxygen of the furanose ring of a number of natural and synthetic nucleosides has been replaced by a methylene group. This transformation changes the furanose ring into a cyclopentane ring. The term carbocyclic nucleoside is used to describe these compounds which are structurally analogous to natural and synthetic nucleosides wherein the furanose ring is replaced by a 5-member carbon ring. It is perhaps more accurate to refer to these compounds as carbocyclic nucleoside isosteres because, strictly speaking, they are not nucleosides. Carbocyclic nucleosides, however, is a convenient term because these compounds undoubtedly exert their biological activity by mimicking the parent nucleosides, although their activities may be different for a variety of reasons. Consistent with the presence of the carbocyclic ring, they are not subject to the action of nucleoside phosphorylases and hydrolases that cleave normal nucleosides. Conformationally, however, the expected similarity in bond lengths and bond angles between the tetrahydrofuran and cyclopentane rings allows these analogues to behave as substrates or inhibitors of the enzymes that activate and interconvert nucleosides and nucleotides in living cells. As a result of this likeness, many of these compounds possess an interesting range of biological activities, particularly in the areas of antiviral and anticancer chemotherapy. The majority of carbocyclic nucleosides known to date are of synthetic origin, although two of the most active compounds are natural products: aristeromycin and neplanocin A.

Several carbocyclic nucleosides were conceived and synthesized prior to the isolation of the carbocyclic adenosine prototype aristeromycin from natural sources. Some of the initially synthesized compounds were simple cyclopentyl substituted bases, but others included true isosteres of thymidine and adenosine. The first reported synthesis of carbocyclic thymidine however, was found to be in error, but the correct compound was later prepared. Most current synthetic approaches begin with the construction of the heterocyclic base from a functionalized cyclopentylamine which, with very few exceptions, is obtained as a racemic mixture. Consequently, most of the reported synthetic carbocyclic nucleosides are racemates. Recently, however, an enantioselective synthesis of aristeromycin and neplanocin A was achieved by Ohno et al., as reported in J. Am. Chem. Soc. 105, 4049 (1983). Of the three total syntheses of neplanocin A reported in 1983, two are enantioselective.

The basic method of synthesis of carbocyclic nucleosides has remained substantially unchanged since Shealy's original work, published in J. Am. Chem. Soc, 88, 3884 (1966), and J. Am. Chem. Soc. 91, 3075 (1969). This synthesis involved:

(1) synthesis of the carbocyclic ribofuranosylamine (C—rib—NH$_2$), and (2) construction of the purine or pyrimidine ring from this amine by well established procedures in nucleoside chemistry. The other syntheses that followed differed mainly in the novelty and efficiency of producing the desired C—rib—NH$_2$ with the correct stereochemical disposition of substituents.

Most of the syntheses used a rigid bicyclo[2.2.1]heptene system, which allowed for better control of the stereochemistry of incoming substituents in subsequent reactions. When nonbornadienes were used as starting materials, the extra carbon atom in the molecule was replaced by the required amino function via a Hoffmann rearrangement of a carboxylic acid amide generated after ozonolysis of one of the double bonds. Later, in an effort to overcome the use of the Hoffmann reaction, azabicyclo[2.2.1]heptene systems, which already contain a latent amine functionality, allowed a more efficient generation of C—rib—NH$_2$. Ohno's use of a chemico enzymatic hydrolysis of a mesodiester allowed synthesis of an enantiomerically pure C—rib—NH₂. Other methods often led to the desired amine only in its racemic form.

Among the various synthetic approaches to purines and pyrimidines, only a few methods have been used in carbocyclic nucleoside chemistry, mainly because of the early commitment to the synthesis via the cyclopentylamine.

To form purines, the time-honored method used has been to convert the carbocyclic amine to the corresponding pyrimidylaminocyclopentane derivative which is then followed by completion of the pyrrole, imidazole, or triazole ring, to give the corresponding purine carbocyclic nucleoside. The reactive 6-chloro substituent allows replacement with ammonia or water to give the adenine and hypoxanthine analogues, respectively. Completion of the bicyclic system varies accordingly; it consists of (1) a spontaneous acid-catalyzed cyclization; (2) formation of the imidazole ring after treatment with an activated one-carbon reagent such as triethylorthoformate; or (3) diazotization of the primary aromatic amine to give the 8-azapurine analogue.

All reported syntheses of carbocyclic pyrimidines have made use of preformed carbocyclic amines as starting materials. The procedures apply the general methodology for the synthesis of uracil and thymine. An acyl isocyanate derivative is reacted with the carbocyclic amine to give an intermediate acryloylurea which is then cyclized in the presence of concentrated ammonia, or with acid catalysts, to give the uracil or thymine analogue. Alternatively, the same result can be obtained by reacting the carbocyclic amine with 3-ethoxy-N,2-bis(ethoxycarbonyl)acrylamide to give the 5-carboethoxyuracil. The 5-substituent was later removed by hydrolysis and decarboxylation. The generated unsubstituted carbocyclic uridine derivatives were amenable to direct halogenation at C-5 and the halogen later displaced by a host of nucleophiles to produce a number of 5-substituted uridine analogues.

Transformation of the uracil ring into cytosine requires conversion of the cyclic amide to the 4-chloropyrimidine, which reacts with ammonia. Alternatively, thiation of the uridine analogue to the corresponding 4-thiouracil derivative, followed by methylation and ammonolysis, produces identical results.

Purine carbocyclic nucleosides include compounds with an intact imidazo[4,5-d]pyrimidine (purine) ring system bearing different 9-cyclopentyl substituents that mimic the several known sugar moieties of the corresponding nucleoside counterparts. Other variations include substitutions at positions 6, 2, and 8.

The first of the ribose isosteres that was synthesized was the saturated carbocyclic analogue of adenosine, C-Ado. C-Ado displayed a wide range of biological activities. It was highly cytotoxic to both H.Ep.-2 and L1210 cells in culture, but it demonstrated poor selectivity towards the tumor cells in view of its inactivity in the in vivo mouse L1210 model system. At subtoxic concentrations, it induced cell proliferation of quiescent normal cells, but in contrast, it inhibited growth in malignant cell lines. The primary toxic effects of C-Ado appear to be mainly derived from the corresponding nucleotide (C-AMP) generated in cells containing adenosine kinase. Like adenosine, C-Ado is also deaminated by adenosine deaminase, but its affinity for the enzyme is a hundredfold lower.

All other 6-substituted C-Ado analogous reported have also been found to be ineffective against L1210 leukemia in mice, despite the fact that some of them were found to be cytotoxic to H.Ep.-2 cells in vitro.

The saturated carbocyclic analogue of 3-deazaadenosine (3-deazaaristeromycin) was first reported in 1982 by Montgomery et al in *J. Med. Chem.* 25, 626 (1982). This compound was found to be a very potent and specific inhibitor of the enzyme which hydrolyzes S-adenosyl-L-homocysteine (AdoHcy). Besides demonstrating good antiviral activity against herpes simplex and vaccinia viruses, it was devoid of some of the undesirable side effects typical of other antiviral agents operating by the same mechanism. The antiviral activity observed for these compounds appears to result from the inhibition of methylation of the 5' cap of viral m-RNA caused by the increase accumulation of AdoHcy inside the cell. Antiviral activity of this nature is discussed by De Clerq et al in *Biochem. Biophys. Res. Commun.* 129, 306 (1985). Inhibition of this critical methylation reaction hinders the translation of viral m-RNA into viral proteins. A common characteristic shared by 3-deazaadenosine and 3-deazaaristeromycin is resistance towards phosphorylation and deamination, which suggests that the carbocyclic structure plays a significant role in conferring the aforementioned selectivity to 3-deazaaristeromycin.

Recently, a different class of carbocyclic nucleosides has become interesting after the isolation and total synthesis of the fermentation antibiotic neplanocin A. Neplanocin A is also a potent inhibitor of AdoHyc hydrolase, but since it is readily phosphorylated, it has a multiplicity of side effects including cytotoxicity. The important structural feature of neplanocin A is the unsaturation present in its cyclopentenyl ring, which gives the molecule unique pharmacologic properties when compared with its saturated counterpart, aristeriomycin.

SUMMARY OF THE INVENTION

It is an object of the present invention to overcome deficiencies in the prior art, such as indicated above.

A further object is to advance the art of antiviral and cancer chemotherapy.

Still a further object is to provide the compound 3-deazaneplanocin A and a method for preparing this compound.

It is another object of this invention to provide a method for preparing cyclopentenyl carbocyclic nucleosides.

The present invention relates to the compound 3-deazaneplanocin A and a method of preparing this compound. 3-Deazaneplanocin A has been found to be a particularly potent inhibitor of AdoHyc hydrolase without the toxicity of neplanocin A.

The synthesis of 3-deazaneplanocin A is a simple procedure using a preformed purine base in a displacement reaction with a readily accessible cyclopentenyl tosylate. Any leaving group can be used on the cycolpentenyl ring rather than a tosylate. The preparation of 3-deazaneplanocin A is given as follows:

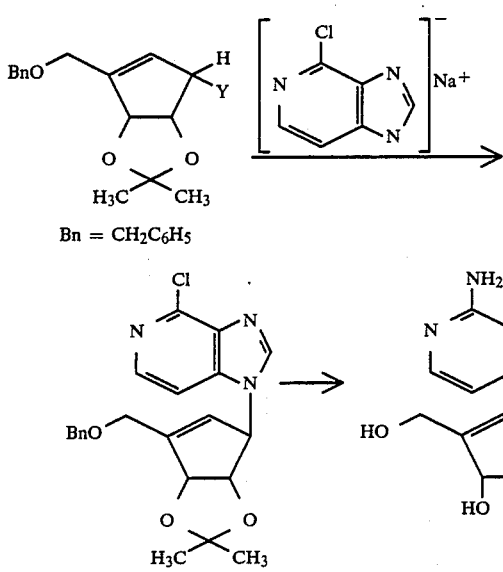

Bn = CH₂C₆H₅ wherein Y can be any leaving group such as hydroxy, acyloxy, mesylate, tosylate, chlorine, bromine, or iodine.

DETAILED DESCRIPTION OF THE INVENTION

Compounds Described

Figure 1:
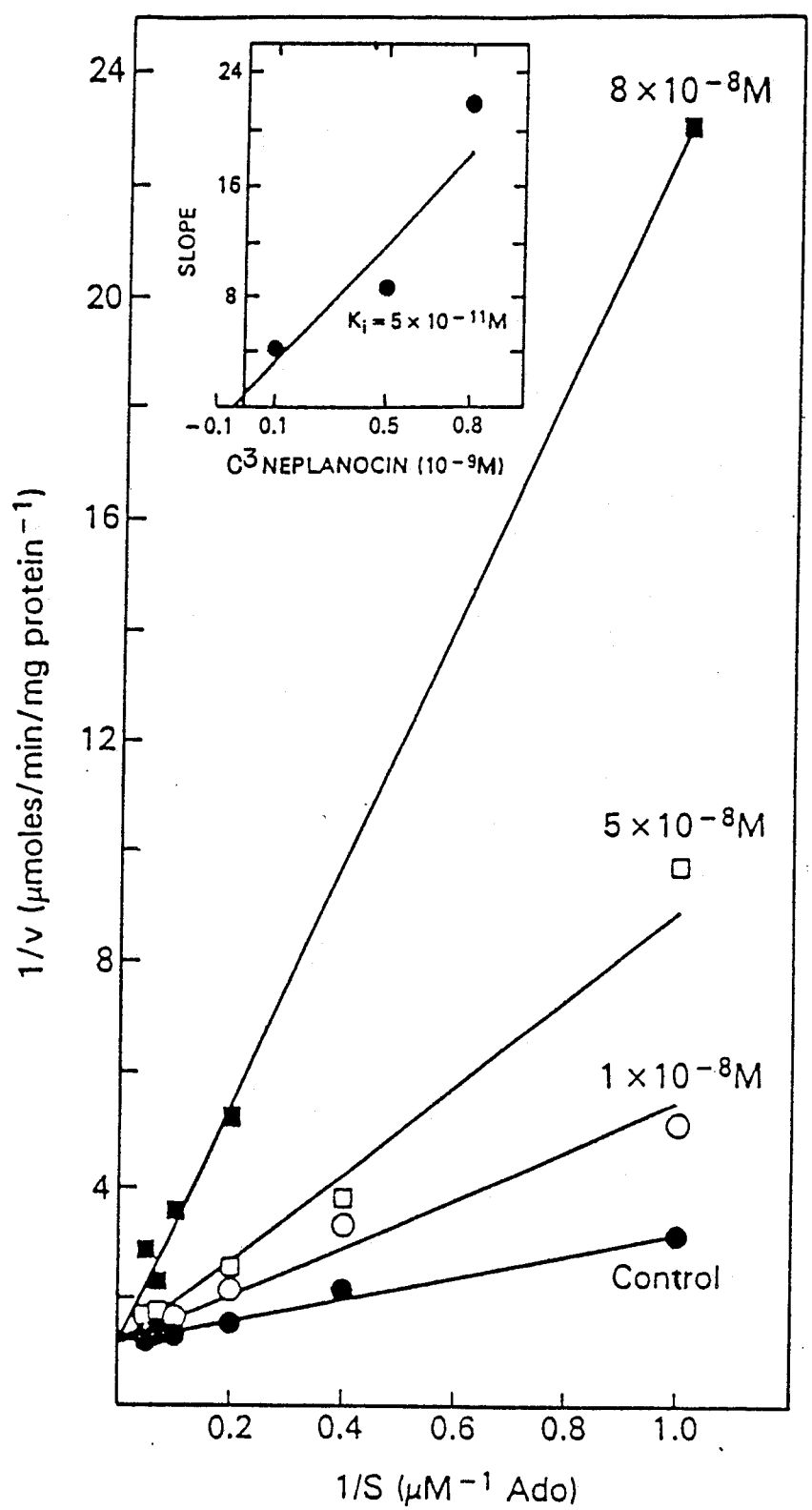
FIG. 1 shows the competitive inhibition by 3-deazaneplanocin A of hamster liver AdoHcy hydrolase.

Using prior art (Lim and Marquez), Tetrahedron Letters, 1983, 24, 5559–62), the stereoselective synthesis of alcohol (Formula 1) was performed. This compound was functionalized to have a reactive leaving group, such as a tosylate (Formula 2, Example A), which constitutes a key step in the simplified methodology to generate cyclopentenyl carbocyclic nucleosides by a direct-displacement reaction (Examples B, E, F, Q and R). The protected compounds obtained from this procedure can then be further manipulated and their protective groups removed to give biologically active compounds such as neplanocin A (Examples C and D), 3-deazaneplanocin A (Examples G and H), 2',3'-dideoxycyclopentenyl cytosine (Examples I through P), etc. These latter transformations are virtually unlimited by the use of conventional organic chemistry and involve the removal, substitution and inversion of the hydroxyl groups at positions 2' and 3' of the cyclopentenyl ring.

Through these procedures the corresponding 2'-deoxy-, 3'-deoxy, ara-, xylo-, lyxo- dideoxy analogues of purine, pyrimidine or other heterocyclic cyclopentenyl nucleosides can be obtained.

An important part in the use of the direct-displacement reaction to obtain these compounds is the determination of the exact site of attachment of the cyclopentenyl moiety to the heterocyclic bases. This has been accomplished by the use of $^{13}$C-NMR spectroscopy or $^{1}$H-NMR Nuclear Overhauser Enhancement (Noe) measurements. The NOE experiments leading to the correct assignment of the structure of 3-deazaneplanocin A as the N-9 isomer are given in Example S using the precursor chloro compound obtained in Example G.

It has been found that cyclopentenyl carbocyclic nucleosides in addition to 3-deazaneplanocin A can be prepared according to the displacement reaction of the present invention. The reaction is as follows, as shown in Equation I.

Equation I

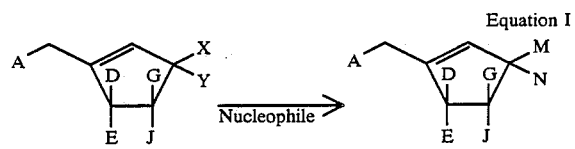

wherein X and Y are selected from the group consisting of =H, OSO₂C₆H₄CH₃; OSO₂CH₃, OSO₂CF₃, F, Cl, Br, I, OCOCH₃, OCOC₆H₅,OH with the premise that X and Y cannot both be H.

A, D, E, G, and J are selected from the group consisting of H, OH, O-alkyl and aryl [including OCH₃, OC(CH₃)₂O, OCH₂C₆H₅, OC(C₆H₅)₃], O-acyl [including OCOC₆H₅, OCOCH₃], O-silyl [including OSi(CH₃)₃, OSi[CH(CH₃)₂]₂ OSi[CH(CH₃)₂]₂O]; O, wherein E and J together or A and E together or D and G together can form a heterocyclic group.

The bases for use in this reaction are selected from the group consisting of purines, pyrimidines, and five and six membered aglycons.

The heterocyclic nucleophiles may be present as a salt or as a free base. The nucleophile may also be a simple nucleophile as such as NaCN, NaN₃, or CH≡CNa.

If the leaving group on the starting material is at position Y, then the product will have the nucleophilic group in position M as shown in Equation I. If the leaving group in the starting material is at position X, then the product will have the nucleophilic group in position N.

The following compounds can be made by the nucleophilic substitution reaction of the present invention:

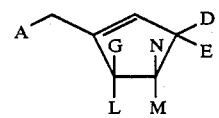

A is Q; O(POQ₂)$_L$ POQ₂ (and Group IA, IIA and Pt salts)
G═Q L═Q N═Q M═Q
N+M═O G+L═O G+N═O L+M═O
L+M═OC(CH₃)₂O
L+A═OSi[CH(CH₃)₂]₂OSi[CH(CH₃)₂]₂O Q is selected from the group consisting of R; O; CR$_2$; OR; NR$_2$; SR; SeR; CN; N$_3$; CR=CR$_2$; C≡CR; CH$_2$POQ$_2$ R is selected from the group consisting of H; (CH$_2$)$_J$CH$_3$; CH$_2$C$_6$H$_5$; C$_6$H$_5$; (C$_6$H$_5$)$_3$C; C$_6$H$_5$CO; CH$_3$(CH$_2$)$_J$CO; Si(CH$_3$)$_3$; Si[CH(CH$_3$)$_2$-]$_2$OSi[CH(CH$_3$)$_2$]$_2$; SO$_2$C$_6$H$_4$CH$_3$; SO$_2$CH$_3$; SO$_2$CF$_3$; F; Cl; Br; I; CN; COQ; CQ$_3$

J=0-20
L=0-2

D is selected from the group consisting of H, Q, and all the purines, pyrimidines and 5-membered aglycons as shown below.

E is selected from the group consisting of H; Q; all the purines, pyrimidines and 5-membered aglycons as shown below.

Purine aglycon portions of the cyclopentenyl nucleosides represented in Equation I of the present invention include

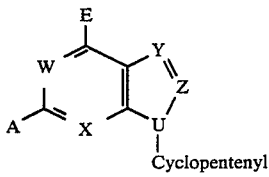
Cyclopentenyl

U=N; CH
W=N; CH
X=N; CH
Y=N; CH; CCONH$_2$; CCN; CE
Z=N; CH; CE

A is selected from the group consisting of G; NG$_2$; OG; SG; SeG

E is selected from the group consisting of G; NG$_2$; OG; SG; SeG

G is selected from the group consisting of H; (CH$_2$)$_J$CH$_3$; CH=CG$_2$; (CH$_2$)$_J$CH=CG$_2$; C≡CG; C$_6$H$_5$; C$_6$F$_5$; CH$_2$C$_6$H$_5$; COC$_6$H$_5$; CO(CH$_2$)$_J$CH$_3$; F; Cl; Br; I; CN; CHO; COOG; COE; CE$_3$; O; (CH$_2$)$_T$; N$_3$; CH$_2$G.

J=0-20
T=1-10

Other compounds that can be made by the process of the present invention include compounds wherein the base is a five-membered aglycon, as shown below:

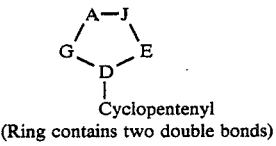
Cyclopentenyl
(Ring contains two double bonds)

A=CH; N; O; S; Se; CCONH$_2$; CCN
J=CH; N; O; S; Se; CCONH$_2$; CCN
G=CH; N; O; S; Se
E=CH; N; O; S; Se
D=C; N

Another group of compounds having antiviral and antitumor activity, that can be made by the process of the present invention, are those wherein the base substituent on the cyclopentenyl group is a pyrimidine algycon, of the following formulae:

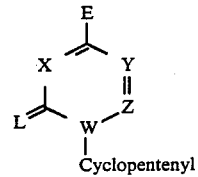
Cyclopentenyl

W=N, CH
X=N; CH
Y=N; CH; CE
Z=N; CH; CE
Y+Z=NHCH$_2$ (with no intervening double bond)
L=O; S; Se
E=G; NG$_2$; OG; SG; SeG;
G=H; (CH$_2$)$_J$CH$_3$; (CH$_2$)$_M$; CH=CG$_2$; (CH$_2$)$_J$CH=CG$_2$; C≡CG; C$_6$H$_5$; C$_6$F$_5$; CH$_2$C$_6$H$_5$; COC$_6$H$_5$; CO(CH$_2$)$_J$CH$_3$; F; Cl; Br; I; CN; CHO; COOG; COE; CE$_3$; O; N$_3$; CH$_2$G

J=0-20
M=1-10

Cyclo-(cyclopentenyl) derivatives that may be prepared according to the process of the present invention:

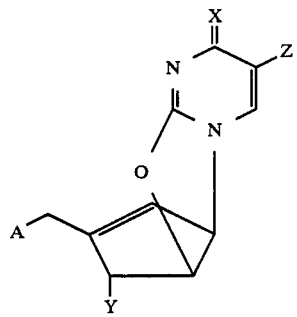

A=H; OH; OR
X=O; NR
Y=H; OH; OR; Z

Z is selected from the group consisting of H; (CH$_2$)$_J$CH$_3$; CF$_3$; NO$_2$; CN; F; Cl; Br; I; CH=CZ$_2$.

R is selected from the group consisting of CO(CH$_2$)$_J$CH$_3$; COC$_6$H$_5$; CH$_2$C$_6$H$_5$; C(C$_6$H$_5$)$_3$; O(-PO$_3$)$_L$PO(OH)$_2$; H

J=0-20
L=0-2

Specific compounds that can be made by the process of the present invention, and which have anti-viral and antitumor activity are as follows:

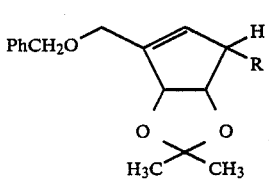

FORMULA 1, R = OH

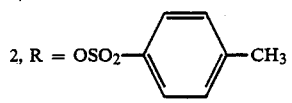
2, R = OSO$_2$—⟨ ⟩—CH$_3$

-continued
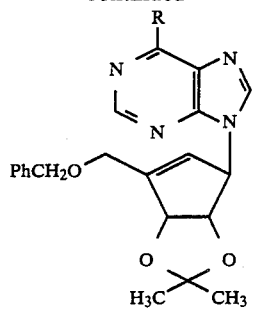
3, R = Cl
4, R = NH₂
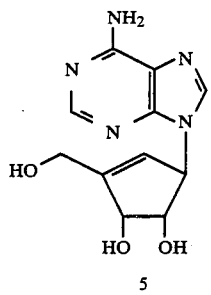
5
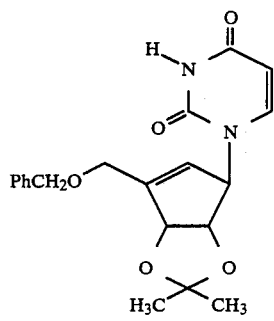
6
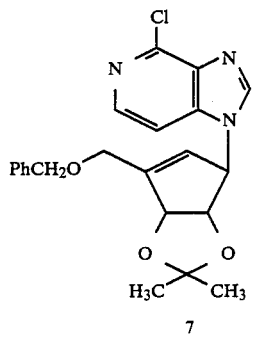
7
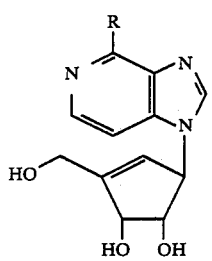
8, R = Cl
9, R = NH₂
-continued
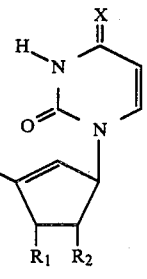
10, R₁ = R₂ = OH; X = O
11, R₁ = R₂ = O—C—O; X = O
              ‖
              S
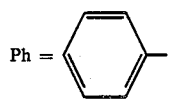
Ph =
12a, R₁ = H; R₂ = OH; X = O
12b, R₁ = OH; R₂ = H; X = O
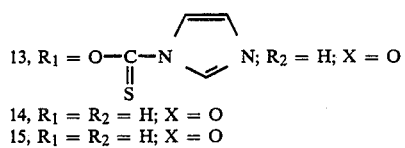
13, R₁ = O—C—N⟩N; R₂ = H; X = O
         ‖
         S
14, R₁ = R₂ = H; X = O
15, R₁ = R₂ = H; X = O
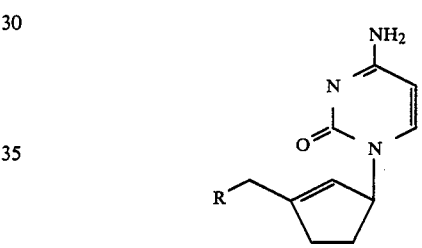
16, R = OCH₂Ph
17, R = OH
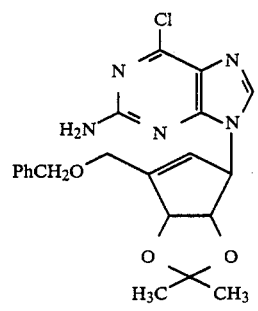
18
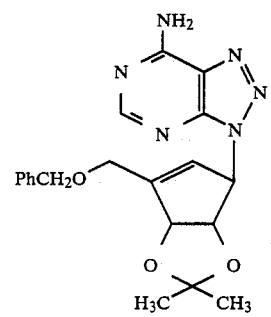
19

-continued

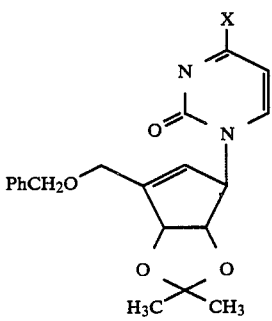

20, X = SH
21, X = NH₂

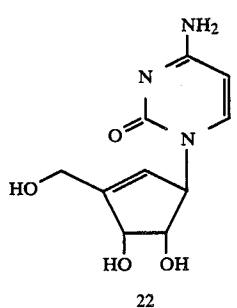

22

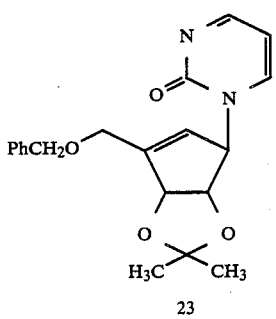

23

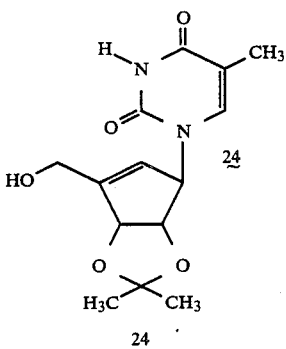

24

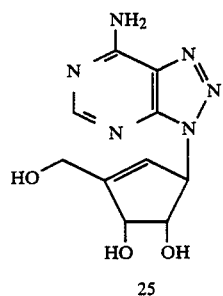

25

-continued

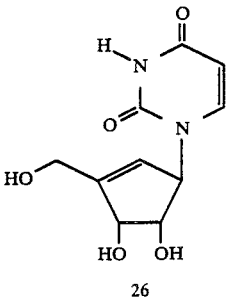

26

The advantage of the displacement reaction for synthesizing these types of carbocyclic nucleosides is that previous methods of synthesizing these compounds required a fifteen-step synthesis process. For example, to prepare neplanocin A, starting with the readily available D(+)-ribonic acid gamma-lactone, 2-cyclopentene-1-one was stereoselectively reduced to the corresponding allylic alcohol possessing the alpha configuration. This compound, in turn, was converted to the versatile 2-cyclopentenylamine after a three-step sequence which included mesylation, $SN_2$ displacement with sodium azide, and reduction. The carbocyclic amine obtained then required four additional steps to complete the 6-aminopurine ring of neplanocin A, and five extra steps to complete the uracil ring of the carbocyclic uridine analogue.

The displacement reaction sequence applied to 3-deazaneplanocin A is described in the three-step reaction sequence shown in Examples F, G, and H.

The new method of synthesizing carbocyclic nucleosides greatly simplifies the preparation of these compounds.

Stereoselective reduction of the cyclopentenyl double bond can be accomplished to produce the saturated carbocyclic compounds (aristeromycin analogs).

The following description of the specific embodiments of the invention will so fully reveal the general nature of the invention that others can, by applying current knowledge, readily modify and/or adapt for various applications such specific embodiments without departing from the generic concept of the invention. Therefore, such adaptations and modifications should and are intended to be comprehended within the meaning and range of equivalent of the disclosed embodiments. It is to be understood that the phraseology or terminology used herein is for the purpose of description and not of limitation.

EXAMPLE A (1S,2S,3R)-4-Benzyloxymethyl-2,3-O-(methylethylidene)-4-cyclopentene-1-ol, p-toluenesulfonate ester (Formula 2)

A solution of alcohol 1 (0.7068 g, 2.56 mmol), triethylamine (1.05 g, 10.4 mmol), and p-toluenesulfonyl chloride (1 g, 5.25 mmol) in 10 ml of dry methylene chloride was stirred overnight at room temperature. The reaction mixture was diluted with 100 ml of methylene chloride, washed with water, dried (MgSO₄), and concentrated in vacuo. Flash column chromatography, using hexane-ethyl acetate (3:2) afforded 0.9 g (82%) of 2 as a white solid, mp 65°-68° C.; ¹H-NMR (CDCl₃) δ 2.27 and 2.29 (singlets, 6H, isopropyl), 2.40 (s, 3H, PhCH₃), 4.10 (d, J=2 Hz, 2H, H-6ₐ,ᵦ), 4.48 (s, 2H, OCH$_2$Ph), 4.67 (dd, J=4 Hz, 1H, H-2), 4.82 (d, J=4 Hz, 1H, H-3), 5.18 (m, 1H, H-1), 5.63 (br s, 1H, H-5), 7.24 (s, 5H, Ph), 7.25 (d, J=8 Hz, 2H, aromatic), 7.80 (d, J=8 Hz, 2H, aromatic).

EXAMPLE B

6-Chloro-9-[(1′R,2′S,3′R)-4′-benzyloxymethyl-2′,3′-O-(methylethylidene)-4′-cyclopenten-1′-yl]-9H-purine (Formula 3)

6-Chloropurine (0.4 g, 2.59 mmol) was added to a stirred suspension of NaH (82 mg as an 80% oil suspension) in 10 ml of dry acetonitrile at room temperature, and stirring was continued for 40 min. The tosylate 2 (0.32 g, 0.743 mmol) was added and the resulting mixture was refluxed for 3 h. After allowing the reaction to cool to room temperature, the mixture was diluted with 100 ml of methylene chloride, filtered, and the filtrate was concentrated in vacuo. Column chromatograpy on silica gel, eluting with hexane-ethyl acetate (1:1), afforded 95 mg (31%) of 3: $^1$H-NMR (CDCl$_3$) δ 1.35 and 1.48 (singlets, 6H, isopropyl), 4.29 (s, 2H, H-6′$_{a,b}$), 4.62 (s, 2H, OCH$_2$Ph), 4.73 (d, J=5.5 Hz, 1H, H-2′), 5.40 (d, J=5.5 Hz, 1H, H-3′), 5.64 (s, 1H, H-1′), 5.83 (d, J=1 Hz, 1H, H-5′), 7.34 (m, 5H, Ph), 8.01 (s, 1H, H-2), 8.75 (s, 1H, H-8).

EXAMPLE C

9-[(1′R,2′S,3′R)-4′-Benzyloxymethyl-2′,3′-O-(methylethylidene)-4′-cyclopenten-1′-yl]adenine (Formula 4)

Method A. A solution of the protected nucleoside 3 (50 mg, 0.12 mmol) was heated in a steel bomb at 70° C. for 5 days in saturated (at 0° C.) methanolic ammonia (100 ml). After the excess ammonia was allowed to escape, the reaction mixture was concentrated in vacuo. Column chromatography on silica gel, eluting with ethyl acetate, afforded 35.6 mg (75%) of 4; $^1$H-NMR (CDCl$_3$) δ 1.36 and 1.48 (singlets, 6H, isopropyl), 4.29 (s, 2H, H-6′$_{a,b}$), 4.63 (s, 2H, OCH$_2$Ph), 4.72 (d, J=5.6 Hz, 1H, H-3′), 5.38 (d, J=5.5 Hz, 1H, H-2′), 5.57 (d, J=1.5 Hz, 1H, H-1′), 5.70 (s, 2H, NH$_2$), 5.82 (m, 1H, H-5′), 7.35 (m, 5H, Ph), 7.67 (s, 1H, H-2), 8.36 (s, 1H, H-8).

Method B. Adenine (0.1265 g, 0.936 mmol) was added to a stirred suspension of NaH (30 mg as an 80% oil suspension) in 5 ml of dry acetonitrile at room temperature, and stirring was continued for 40 min. The tosylate 2 (0.2687 g, 0.625 mmol) was added and the resulting mixture was stirred at 70° C. for 24 h. After allowing the reaction mixture to cool to room temperature, the mixture was diluted with 50 ml of methylene chloride, filtered and the solvent was concentrated in vacuo. Column chromatography on silica gel, eluting with ethyl acetate and 10% methanol in ethyl acetate, gave 32 mg (8.6%) of 4.

EXAMPLE D

9-[(1′R,2′S,3′R)-4-Hydroxymethyl-2′,3′-dihydroxy-4-cyclopenten-1′-yl]adenine (Formula 5). Neplanocin A.

Boron trichloride (1.3 ml of a 1M solution in methylene chloride, 1.3 mmol) was added to a solution of the protected Neplanocin A(4) (0.108 g, 0.274 mmol) in dry methylene chloride (8 ml) at −78° C. The reaction mixture was stirred for an additional 3 h at −78° C. followed by the addition of 60 ml of methanol. The solvent was removed in vacuo and another 60 ml of methanol was added to the residue. The solvent was again removed in vacuo. The residue was partitioned between water and ethyl acetate and the aqueous layer was lyophilized to afford a solid. Chromatography on a C-18 reversed-phase Sep-Pak ® cartridge, eluting with water, gave 45.5 mg (63%) of 5 which was recrystalized from methanol; mp 222°–225° C.; $^1$H-NMR (D$_2$O) δ 4.16 (s, 2H, H-6′$_{a,b}$), 4.35 (dd, J=5.5 Hz, H-2′), 4.49 (d, J=5.5 Hz, H-3′), 5.47 (m, 1H, H-1′), 5.75 (d, J=1.5 Hz, 1H, H-5′), 8.27 (s, 1H, H-8), 8.35 (s, 1H, H-2).

EXAMPLE E

1-[(1′R,2′S,3′R)-4′-Benzyloxymethyl-2′,3′-O-(methylethylidene)-4′-cyclopenten-1′-yl]-2,4(1H,3H)pyrimidinedione (Formula 6)

A mixture of uracil (80 mg, 0.714 mmol), the tosylate 2 (100 mg, 0.232 mmol) and anhydrous potassium carbonate (108 mg) was stirred in anhydrous DMSO (2 ml) at room temperature for 36 h. Water was added and the mixture was extracted with chloroform. The organic layer was dried and concentrated to give an oily residue. Chromatography on preparative TLC silica gel plates, eluting with ethyl acetate, gave 22.5 mg (26%) of 6. $^1$H-NMR (CDCl$_3$) δ 1.35 and 1.43 (singlets, 6H, isopropyl), 4.23 (s, 2H, H-6′$_{a,b}$), 4.60 (m, 3H, H-2′ and OCH$_2$Ph), 5.20 (d, J=5.2 Hz, 1H, H-3′), 5.39 (s, 1H, H-1′), 5.66 (m, 2H, H-5 and H-5′), 7.00 (d, J=8 Hz, 1H, H-6), 7.35 (s, 5H, Ph).

EXAMPLE F

4-Chloro-1-[(1′R,2′S,3′R)-4′-benzyloxymethyl-2′,3′-O-(methylethylidene)-4′-cyclopenten-1′-yl]imidazo[4,5-c]pyridine (Formula 7)

6-Chloro-3-deazapurine (30 mg, 0.195 mmol) was added to a suspension of NaH (7.5 mg as an 80% oil suspension) in anhydrous acetonitrile (2 ml) at room temperature. The resulting mixture was stirred at room temperature for 40 min before the tosylate 2 (0.126 g, 0.29 mmol) was added. After refluxing for 5 h, the mixture was cooled, diluted with methylene chloride, and the insoluble material was removed by filtration. The filtration was concentrated to yield 47.4 mg (59%) of crude product as a mixture of N-7 and N-9 substituted isomers, from which 26.2 mg (33%) of the desired and less polar N-9 isomer was obtained after chromatography on a silica gel column (ethyl acetate-hexane, 1:1) as a foam; $^1$H-NMR (CDCl$_3$) δ 1.34 and 1.49 (singlets, 6H, isopropyl), 4.30 (s, 2H, H-6′$_{a,b}$), 4.56 (d, J=5.8 Hz, 1H, H-2′), 4.66 (s, 2H, OCH$_2$Ph), 5.28 (d, J=5.8 Hz, 1H, H-3′), 5.39 (br s, 1H, H-1′), 5.96 (br s, 1H, H-5′), 7.40 (d, J=5.4 Hz, 1H, H-3), 7.42 (m, 5H, Ph), 7.90 (s, 1H, H-8), 8.23 (d, J=5.4 Hz, 1H, H-2).

EXAMPLE G

4-Chloro-1-[(1′R,2′S,3′R)-4′-hydroxymethyl-2′,3′-dihydroxy-4′-cyclopenten-1′-yl]imidazol[4,5-c]pyridine (Formula 8)

Boron trichloride (0.5 ml of a 1M solution in methylene chloride, 0.5 mmol) was added to a solution of the protected compound 7 (20 mg, 0.05 mmol) in dry methylene chloride (1 ml) at −78° C. for 3 h. Methanol (10 ml) was added and the mixture was concentrated to dryness. Another portion of methanol was added and again evaporated. The residue was partitioned between water and ethyl acetate. The aqueous layer was lyophilized to afford a solid (11.3 g, 82%). Flash chromatography on a C-18 column, eluting with 20% methanol in water, gave the purified product as a white solid after lyophilization, mp 219°–220° C.; $^1$H-NMR (DMSO-$_6$) δ 4.03 (dd, J=5.6 Hz, 1H, H-2'), 4.14 (s, 2H, H-6'$_{a,b}$), 4.38 (d, J=5.6 Hz, 1H, H-3'), 5.40 (m, 1H, H-1'), 5.83 (br s, 1H, H-5'), 7.63 (d, J=5.8 Hz, 1H, H-3), 8.11 (d, J=5.8 Hz, 1H, H-2), 8.36 (s, 1H, H-8).

EXAMPLE H

4-Amino-1-[(1'R,2'S,3'R)-4'-hydroxymethyl-2',3'-dihydroxy-4'-cyclopenten-1'-yl]imidazo[4,5-c]pyridine (Formula 9). 3-Deazaneplanocin A.

The cyclopentenyl 6-chloro-3-deazapurine 8 (11 mg, 0.039 mmol) was heated with anhydrous hydrazine (0.5 ml) at 100° C. for 1 h. The solution was concentrated in vacuo to give a glassy residue. To this residue degased water was added (1 ml) followed by Raney nickel (100 mg), and the resulting mixture was refluxed for 1 h. The catalyst was filtered off and the filtrate was subjected to a C$_{18}$ reversed-phase flash column chromatography, eluting with 20% methanol in water to give 7 mg (70%) of 3-deazaneplanocin as a lyophilized powder; $^1$H-NMR (D$_2$O) δ 4.35 (m, 1H, H-2'), 4.41 (s, 2H, H-6'$_{a,b}$), 4.69 (d, J=5.6 Hz, 1H, H-3'), 5.53 (m, 1H, H-1'), 6.09 (br s, 1H, H-5'), 7.21 (d, J=7.4 Hz, 1H, H-3), 7.65 (d, J=7.4 Hz, 1H, H-2), 8.31 (s, 1H, H-8). The UV spectrum of 3-deazaneplanocin (λ max 262, pH 7) was, as expected, superimposable on that of 3-deazaaristeromycin. MS (FAB, positive mode), m/z (rel. intensity) 263 (MH$^+$, 36.7), 135 (b+2H, 21.6); High resolution FAB MS, m/z 263.112 (MH$^{30}$, calcd. 263.224); [α]$_D^{24}$ −13.5° (c 0.112, H$_2$O).

EXAMPLE I

1-[(1'R,2'S,3'R)-4'-Benzyloxymethyl-2',3'-dihydroxy-4'-cyclopenten-1'-yl]-2,4(1H,3H)-pyrimidinedione (Formula 10)

To a stirred solution of 6 (1.5 g, 4 mmol) in methanol (75 ml) was added cation exchange resin (24 g, 30 equiv., Bio-Rad AG 40W-X8), pre-washed in methanol. The mixture was stirred at 50° for 16 h, followed by filtration, concentration of the methanolic solution, and purification via flash column chromatography (Bio-Rad Bio-Sil A, 200–400 mesh), eluting first with 15:1 CH$_2$Cl$_2$:MeOH and then 10:1 CH$_2$Cl$_2$:MeOH to give 10 as a white foam (1.25 g, 95%); $^1$H-NMR (Acetone-d$_6$) δ 4.22 (m, 3H, H-6'$_{a,b}$ and H-2'), 4.60 (m, 3H, OCH$_2$Ph and H-3'), 5.45 (br s, 1H, H-1'), 5.58 (d, J=6 Hz, 1H, H-5), 5.78 (d, J<1 Hz, 1H, H-5'), 7.34 (d, J=6 Hz, 1H, H-6), 7.36 (m, 5H, Ph).

EXAMPLE J

1-[(1'R,2'S,3'R)-4'-Benzyloxymethyl-2',3'-O-thiocarbonate-4'-cyclopenten-1'-yl]-2,4(1H,3H)-pyrimidinedione (Formula 11)

To a stirred solution of 10 (1.03 g, 3.1 mmol) in dry DMF (25 ml) was added thiocarbonyldiimidazole (0.837 g, 1.5 equiv). The resulting yellow solution was stirred at room temperature for 40 h under nitrogen, followed by concentration under reduced pressure. The residue was taken up in dichloromethane and chromatographed (Kieselgel 60, 70–230 mesh) via gravity column chromatography, eluting with 10:1 CH$_2$Cl$_2$:MeOH. Recrystallization from dichloromethane afforded 1.0 g (87%) of 3, as a white crystalline material, mp >130° C.; $^1$H-NMR (Acetone-d$_6$) δ 4.32 (m, 2H, H-6'$_{a,b}$), 4.62 (dd, J=20 Hz, J'=14 Hz, 2H, OCH$_2$Ph), 5.46 (s, 1H, H-1'), 5.62 (d, J=6 Hz, 1H, H-5), 5.77 (d, J=4 Hz, 1H, H-2'), 6.14 (s, 1H, H-5'), 6.16 (d, J=4 Hz, 1H, H-3'), 7.40 (m, 5H, Ph), 7.58 (d, J=6 Hz, 1H, H-6).

EXAMPLE K

1-[(1'R,2'S)-4'-Benzyloxymethyl-2'-hydroxy-4'-cyclopenten-1'-yl]-2,4-(1H,3H)pyrimidinedione and 1-[(1'R,3'R)-4'-Benzyloxymethyl-3'-hydroxy-4'-cyclopenten-1'-yl]-2,4(1H,3H)pyrimidinedione (Formulas 12a,b)

To a stirred solution of 11 (0.993 g, 2.66 mmol) in dry toluene (30 ml) were added azoisobutyronitrile (0.765 g, 1.75 equiv) and tributyltin hydride (2.2 ml, 3 equiv). The resultant solution was refluxed for 1 hr, cooled, concentrated under reduced pressure, and the residue was dissolved in dichloromethane for purification on a gravity column (Kieselgel-60, 70–230 mesh), eluting with 10:1 CH$_2$Cl$_2$:MeOH to give 835 mg (100%) of 12a and 12b as foams. TLC in 10:1 CH$_2$Cl$_2$:MeOH distinctly revealed the presence of both monohydroxyl compounds.

Compound 12a - $^1$H-NMR (CDCl$_3$) δ 2.48 (dd, J=16 Hz, J'=6 Hz, 1H, H-2' β), 2.96 (dd, J=16 Hz, J'=7 Hz, 1H, H-2' α), 4.09 (s, 2H, H-6'$_{a,b}$), 4.56 (s, 2H, OCH$_2$Ph), 4.92 (m, 2H, H-1' and H-3'), 5.69 (d, J=6 Hz, 1H, H-5), 5.79 (s, 1H, H-5'), 7.12 (d, J=6 Hz, 1H, H-6), 7.35 (s, 5H, Ph), 9.20 (s, 1H, NH).

Compound 12b - $^1$H-NMR (CDCl$_3$) δ 2.40 (br d, J=18 Hz, 1H, H-3' α), 2.83 (dd, J=17 Hz, J'=8 Hz, 1H, H-3' β), 4.10 (s, 2H, H-6'$_{a,b}$), 4.40 (m, 1H, H-2'), 4.57 (s, 2H, OCH$_2$Ph), 5.38 (s, 1H, H-1'), 5.52 (s, 1H, H-5'), 5.64 (d, J=6 Hz, 1H, H-5), 7.15 (d, J=6 Hz, 1H, H-6), 7.35 (s, 5H, Ph), 9.78 (br s, 1H, NH).

EXAMPLE L

1-[(1'R,3'R)-4'-Benzyloxymethyl-3'-O-(1-imidazolyl)-thiocarbonyl-4'-cyclopenten-1'-yl]-2,4(1H,3H)pyrimidinedione (Formula 13)

To a stirred solution of 12a and 12b (0.817 g, 2.5 mmol) in dry DMF (25 ml) was added thiocarbonyldiimidazole (0.695 g, 1.5 equiv). The resulting yellow solution was stirred at room temperature for 40 hr under nitrogen, whereupon TLC (10:1 CH$_2$Cl$_2$:MeOH) revealed total disappearance of starting materials, the presence of the less polar product, and also the presence of an unexpected polar compound. Removal of DMF was followed by flash column chromatography (eluant, ethyl acetate) to give 658 mg (60%) of specifically one monothiocarbonylimidazole species (13). NMR analysis of the polar component, via selective proton irradiation studies, enabled the definite assignment of that material as the 2,2'-anhydronucleoside, arising from the 3'-deoxy starting material. Compound 13 was obtained as a foam; $^1$H-NMR (CDCl$_3$) δ 2.60 (d, J=12 Hz, 1H, H-2' β), 3.27 (dd, J=16 Hz, J'=8 Hz, 1H, H-2' α), 4.14 (s, 2H, H-6'$_{a,b}$), 4.60 (s, 2H, OCH$_2$Ph), 5.63 (br s, 1H, H-1'), 5.76 (m, 2H, H-5 and H-3'), 5.90 (br s, 1H, H-5'), 7.04, 7.63, 8.02 (singlets, 3H, imidazole), 7.13 (d, J=6 Hz, 1H, H-6), 7.36 (s, 5H, Ph), 8.36 (s, 1H, N-H).

EXAMPLE M

1-[(1'R)-4'-Benzyloxymethyl-4'-cyclopenten-1'-yl]-2,4(1H,3H)pyrimidinedione (Formula 14)

To a stirred solution of 13 (0.611 g, 1.44 mmol) in dry toluene (20 ml) were added azoisobutyronitrile (0.415 g, 1.75 equiv) and tributyltin hydride (1.2 ml, 3 equiv). The resultant solution was refluxed for 1 hr, cooled and concentrated under reduced pressure; the residue was taken up in ethyl acetate and purified by gravity column chromatography (eluant, ethyl acetate) to give 6 (287 mg, 67%) of 14 as a foam; $^1$H-NMR (CDCl$_3$) δ 1.70 (m, 1H, H-2' α) 2.52 (m, 3H, H-3' α, 3' β, 2' β), 4.12 (s, 2H, H-6'$_{a,b}$), 4.56 (s, 2H, OCH$_2$Ph), 5.56 (m, 1H, H-1'), 5.67 (d, J=6 Hz, 1H, H-5 and m, 1H, H-5'), 7.12 (d, J=6 Hz, 1H, H-6), 7.34 (s, 5H, Ph), 9.18 (br s, 1H, N-H).

EXAMPLE N

1-[(1'R)-4'-Benzyloxymethyl-4'-cyclopenten-1'-yl]-4-thio-2(1H,3H)pyrimidinone (Formula 15)

To a solution of 14 (0.287 g, 0.96 mmol) in dry benzene (20 ml) was added with stirring 2,4-bis(4-methoxyphenyl)-1,3-dithia-2,4-diphosphetane-2,4-disulfide (Lawesson reagent) (0.505 g, 1.3 equiv). The mixture was refluxed between 0.75–1 hr under Argon, whereupon TLC in 3:7 ethyl acetate:petroleum ether revealed total consumption of starting material. Removal of benzene under reduced pressure, followed by flash column chromatography (eluting first with 1:5 ethyl acetate:petroleum ether and then 1:3 of the same solvent mixture) gave 160 mg (53%) of 15 as a yellow foam; $^1$H-NMR (CDCl$_3$) δ 1.72 (m, 1H, H-2' α), 2.54 (m, 3H, H-3' α, 3' β, 2' β), 4.14 (s, 2H, H-6'$_{a,b}$), 4.58 (s, 2H, OCH$_2$Ph), 5.58 (m, 1H, H-5'), 5.64 (m, 1H, H-1'), 6.37 (dd, J=6 Hz, J' <1 Hz, 1H, H-5), 6.98 (d, J=6 Hz, 1H, H-6), 7.36 (s, 5H, Ph), 9.71 (br s, 1H, N-H).

EXAMPLE O

4-Amino-1-[(1'R)-4'-Benzyloxymethyl-4'-cyclopenten-1'-yl]-2(1H)pyrimidinone (Formula 16)

The thiouracil analog 15 (0.095 g, 0.3 mmol) was heated in methanolic ammonia (25 ml) in a sealed pressure bottle at 80° for 20 h. TLC in 10:1 CH$_2$Cl$_2$:MeOH revealed nearly complete conversion to 16. Evaporation of ammonia and concentration of the crude material was followed by purification via prep TLC (2000 μ) in 10:1 CH$_2$Cl$_2$:MeOH to give 19 mg of recovered starting material and 45 mg (62%) of 16 obtained as a foam; $^1$H-NMR (CDCl$_3$) δ 1.66 (m, 1H, H-2' α) 2.54 (m, 3H, H-3' α, 3' β, 2' β) 4.14 (s, 2H, H-6'$_{a,b}$), 4.56 (s, 2H, OCH$_2$Ph), 5.60 (s, 1H, H-1'), 5.75 (d, J=5 Hz, 1H, H-5 and m, 1H, H-5'), 7.25 (d, J=5 Hz, 1H, H-6), 7.34 (s, 5H, Ph).

EXAMPLE P

4-Amino-1-[(1'R)-4'-hydroxymethyl-4'-cyclopenten-1'-yl]-2(1H)pyrimidinone (Formula 17)

To a solution of 16 (0.036 g, 0.12 mmol) in dry dichloromethane (1.5 ml), chilled to −78°, was added fresh boron trichloride (1M in dichloromethane, 3 equiv). The mixture was stirred for 1 h at −78° whereupon TLC (10:1 CH$_2$Cl$_2$:MeOH) revealed the completion of the reaction. Excess boron trichloride was quenched by the addition of methanol (5 ml×3) followed by evaporation (×3). The cream colored crude foam was purified via reversed phase column chromatography, eluting with 20% methanol to obtain the desired 2',3'-dideoxycyclopentenyl cytosine 17 in 70% yield; $^1$H-NMR (D$_2$O) δ 1.69 (m, 1H, H-2' α) 2.42 (m, 3H, H-3' α, 3' β, 2' β), 4.21 (s, 2H, H-6'$_{a,b}$), 5.51 (br s, 2H, H-1' and H-5'), 5.91 (d, J=6 Hz, 1H, H-5), 7.45 (d, J=6 Hz, 1H, H-6).

EXAMPLE Q

2-Amino-6-chloro-9-[(1'R,2'S,3'R)-4'-benzyloxymethyl-2',3'-O-(methylethylidene)-4'-cyclopenten-1'-yl]-9H-purine (Formula 18)

A mixture of the cyclopentenyl tosylate 2 (0.25 g, 0.58 mmol), 2-amino-6-chloropurine (0.212 g, 1.25 mmol, 2.2 eq), and K$_2$CO$_3$ (~1 g) was suspended in 2 mL of DMSO and stirred at room temperature for 42 h. The suspension was then poured into CH$_2$Cl$_2$ and washed with dilute NaCl. Evaporation of the CH$_2$Cl$_2$ gave an oil which was further dried under high vacuum to remove residual DMSO. Purification by preparative TLC (silica, 3:2 EtOAc:Hexane) gave two major purine containing products of which the faster moving and predominant was the desired N-9 alkylated purine 18 (0.117 g, 47%), mp 137°–140°; $^1$H-NMR (CDCl$_3$) δ 1.35 (s, 3H, CH$_3$), 1.46 (s, 3H, CH$_3$), 4.27 (s, 2H, H-6'$_{a,b}$), 4.61 and 4.62 (2H, PhCH$_2$), 4.67 (d, J=5.3 Hz, 1H, H-2'), 5.10 (br s, 2H, NH$_2$, exchangeable), 5.36 (d, J=5.3 Hz, 1H, H-3'), 5.43 (br s, 1H, H-1'), 5.78 (br s, 1H, H-5'), 7.34 (m, 5H, Ph), 7.65 (s, 1H, H-8); $^{13}$C-NMR (CDCl$_3$) δ 25.8 (CH$_3$), 27.2 (CH$_3$), 64.3 (C-1'), 66.2 (C-6'), 72.8 (PhCH$_2$), 83.7 (C-2'), 83.9 (C-3'), 112.4 (methylethylidene C), 122.7 (C-5'), 125.2 (d, J=12.6 Hz, C-5), 127.3 (Ph), 127.5 (Ph), 128.1 (Ph), 128.2 (Ph), 137.6 (Ph), 140.1 (dd, J=210 Hz, J'=4.4 Hz, C-8), 149.2 (C-4'), 151.0 (s, C-6), 153.2 (dd, J=4.7 Hz, J'=3.1 Hz, C-4), 159.1 (s, C-2).

The minor product was identified as the N-7 isomer: $^1$H NMR-(CDCl$_3$) δ 1.33 (s, 3H, CH$_3$), 1.44 (s, 3H, CH$_3$), 4.27 (s, 2H, H-6'$_{a,b}$), 4.60 (d, J=5.5 Hz, 1H, H-2'), 4.63 (s, 1H, PhCH$_2$), 5.21 (d, J=5.5 Hz, 1H, H-3'), 5.36 (br s, 2H, NH$_2$, exchangeable), 5.84 (br s, 1H, H-1'), 5.91 (br s, 1H, H-5'), 7.35 (m, 5H, Ph), 7.84 (s, 1H, H-8); $^{13}$C-NMR (CDCl$_3$/D$_2$O) δ 23.9 (CH$_3$), 27.3 (CH$_3$), 66.5 (C-1'), 66.6 (C-6'), 73.3 (PhC*H$_2$), 83.4 (C-2'), 84.7 (C-3'), 112.7 (methylethylidene C), 116.3 (dd, J=4.9 Hz, J'=1.5 Hz, C-5), 121.9 (C-5'), 127.5 (Ph), 127.8 (Ph), 128.4 (Ph), 137.7 (Ph), 143.9 (s, C-6), 145.7 (dd, J=209 Hz, J'=4.5 Hz, C-8), 150.9 (C-4'), 159.6 (s, C-2), 164.4 (d, J=13.0 Hz, C-4).

EXAMPLE R

7-Amino-3-[1'R,2'S,3'R)-4'-benzyloxymethyl-2',3'-O-(methylethylidene)-4'-cyclopenten-1'-yl]-3H-1,2,3-triazolo[4,5-d]pyrimidine (Formula 19)

The cyclopentenyl tosylate 2 (0.68 g, 1.58 mmol) and 8-azaadenine (0.62 g, 4.54 mmol, 2.9 eq) were combined in a small round bottomed flask, an excess of K$_2$CO$_3$ (~2 g) was added, and the reaction mixture was suspended in 6 mL of DMSO. After the reaction mixture had stirred at room temperature for 20 h, the suspension was poured into CH$_2$Cl$_2$ and washed with dilute NaCl. Removal of the CH$_2$Cl$_2$ under vacuum was followed by high vacuum removal of residual DMSO. Purification on preparative TLC (silica, 3:2 EtOAc:Hexane) gave two base containing products of which the faster moving was the desired product (39 mg, 7%); $^1$H-NMR (CDCl$_3$/D$_2$O) δ 1.37 (s, 3H, CH$_3$), 1.49 (s, 3H, CH$_3$), 4.28 (s, 2H, H6'$_{a,b}$), 4.59 and 4.60 (2H, PhCH$_2$), 4.97 (d, J=5.6 Hz, 1H, H-2'), 5.49 (d, J=5.6 Hz, 1H, H-3'), 5.87 (br s, 1H, H-1'), 5.97 (br s, 1H, H-5'), 6.69 (br s, 2H, NH$_2$, exchangeable), 7.32 (m, 5H, Ph), 8.50 (s, 1H, H-2); $^{13}$C-NMR (CDCl$_3$/D$_2$O) δ 25.9 (CH$_3$), 27.5 (CH$_3$), 66.4 (C-6'), 67.8 (C-1'), 72.8 (PhC*H$_2$), 83.9 (C-2'), 84.5 (C3'), 112.6 (methylethylidene C), 123.7 (C-5'), 124.6 (s, C-5), 127.9 (Ph), 128.4 (Ph), 138.0 (Ph), 148.6 (C-4'), 148.9 (dd, J=10.2 Hz, J'=2.5 Hz, C-4), 155.8 (d, J=11.2 Hz, C-6), 156.5 (d, J=202.5 Hz, C-2).

EXAMPLE S

NOE experiments with 4-chloro-1-[(1'R,2'S,3'r)-4'hydroxymethyl-2',3'-dihydroxy-4'-cyclopenten-1'-yl]imidazo[4,5-c]pyridine (Formula 8)

Through space interactions between purine protons and cyclopentenyl protons were examined by irradiation (0.032 Watt) of the aglycon protons and integration of the signals corresponding to carbocyclic protons. An enhancement of 1.03 was considered to be experimentally significant. Irradiation at H-8 produced an enhancement of 1.11 of the anomeric (H-1') signal. Irradiation of H-2 enhanced only H-3 (1.10), while irradiation of H-3 enhanced H-2 (1.20), H-1' (1.10), and H-2' (1.03). These results are in agreement with the structure for the N-0 isomer. As anticipated for the N-7 isomer, neither irradiation of H-2 nor H-3 produced any enhancement of the carbocyclic proton signals.

EXAMPLE T 4-amino-1-[(1'R,2'S,3'R)-4'-hydroxymethyl-4'-cyclopenten-1'-yl]-2(1H)pyrimidinone (Formula 22)

Employing the similar type of chemistry that permitted the conversion of compound formula 14 to compound formula 17 (Examples M through P), compound formula 6 was sequentially converted to the corresponding 4-thio compound (formula 20), the 4-amino compound (formula 21) and the final cyclopentenyl cytosine derivative (formula 22) after the removal of the blocking groups. The conversion of compound formula 6 to compound formula 20 proceeded in 58% yield; NMR (CDCl$_3$) δ 1.35 and 1.47 (singlets, 6H, isopropyl), 4.25 (s, 2H, H-6'$_{a,b}$), 4.62 (br s, 3H, OCH$_2$Ph and H-2'), 5.25 (d, J=5.5 Hz, 1H, H-3'), 5.30 (br s, 1H, H-1'), 5.60 (br s, 1H, H-5'), 6.38 (d, J=7.5 Hz, 1H, H-5), 6.81 (d, J=7.5 Hz, 1H, H-6), 7.37 (br s, 5H, Ph), 10.4 (br s, 1H, NH).

The conversion of compound formula 20 to compound formula 21 proceeded in 86% yield; NMR (CDCl$_3$) δ 1.38 and 1.45 (singlets, 6H, isopropyl), 4.25 (s, 2H, H-6'$_{a,b}$), 4.62 (br s, 3H, OCH$_2$Ph and H-3'), 5.20 (s, 1H, H-1'), 5.25 (d, J=5.5 Hz, 1H, H-3'), 5.62 (s, 1H, H-5'), 5.80 (d, J=7.5 Hz, 1H, H-5), 7.13 (d, J=7.5 Hz, 1H, H-6), 7.20 (br s, 5H, Ph).

The conversion of compound formula 21 to compound formula 22 proceeded in 73% yield to give a white solid, mp 138°-141° C.; [α]$_D^{25}$ −104.5° (C 0.13, H$_2$O); NMR (D$_2$O) δ 4.12 (t, J=6 Hz, 1H, H-2'), 4.30 (s, 2H, H-6'$_{a,b}$), 4.60 (d, J=6 Hz, 1H, H-3'), 5.45 (br s, 1H, H-1'), 5.81 (d, J<1 Hz, 1H, H-5'), 6.00 (d, J=7.3 Hz, 1H, H-5), 7.22 (d, J=7.3 Hz, 1H, H-6), MS (FAB, positive mode), M/Z 240 (MH+).

EXAMPLE U

1-[(1'R,2'S,3'R)-4'-Benzyloxymethyl-2',3'-O-(methylethylidene)-4'-cyclopenten-1'-yl]-2(1H)pyrimidinone (Formula 23)

A solution of alcohol 1 (236 mg, 0.85 mmol), triphenyl phosphine (224 mg, 0.85 mmol), and diethyl azodicarboxylate (148.7 mg, 0.85 mmol) in dry DMF (5 ml) was reacted with 2(1H)pyrimidinone (70 mg, 0.85 mmol) dissolved in 1 ml of dry DMF and the resulting mixture stirred at room temperature for two days. After removing the solvent in vacuo, the residue was prepurified by passing it through a short silica gel column eluted first with benzene and then with CH$_2$Cl$_2$ in order to remove a polar impurity. The collected material was then purified by reverse phase HPLC chromatography on a C-18 column using 10% aqueous methanol to afford 63 mg (22%) of pure 23 as a foam; NMR (CDCl$_3$) δ 1.38 and 1.44 (singlets, 6H, isopropylidene), 4.20 (s, 2H, H-6'$_{a,b}$), 4.60 (s, 2H, OCH$_2$Ph), 4.80 (d, J=6 Hz, 1H, H-3'), 5.25 (d, J=6 Hz, 1H, H-2'), 5.85 (s, 1H, H-1'), 6.00 (s, 1H, H-5'), 6.95 (t, J=4.8 Hz, 1H, H-5), 7.30 (br s, 5H, Ph), 8.52 (d, J=4.8 Hz, 2H, H-4 and H-6).

EXAMPLE V

5-Methyl-1-[(1'R,2'S,3'R)-4'-benzyloxymethyl-2',3'-O-(methylethylidene)-4'-cyclopenten-1'-yl]-2,4(1H,3H)pyrimidinedione (Formula 24)

A mixture of thymine (45 mg, 0.35 mmol), the tosylate 2 (50 mg, 0.116 mmol) and anhydrous potassium carbonate (54 mg) was stirred in anhydrous DMSO (1 ml) at room temperature for 36 h. After this time, the mixture was diluted with water (50 ml) and extracted four times with CH$_2$Cl$_2$. The combined organic extracts were reduced to dryness and chromatographed on preparative TLC silica gel plates with ethyl acetate to give 6 mg (13.4%) of 24; $^1$H-NMR (CDCl$_3$) δ 1.34 and 1.44 (singlets, 6H, isopropyl), 1.88 (s, 3H, CH$_3$), 4.22 (s, 2H, H-6'$_{a,b}$), 4.56 (br s, 3H, OCH$_2$Ph and H-2'), 5.20 (d, J=6 Hz, 1H, H-3'), 5.38 (s, 1H, H-1'), 5.62 (s, 1H, H-5'), 6.78 (s, 1H, H-6), 7.34 (br s, 5H, Ph), 8.52 (br s, 1H, NH).

EXAMPLE W

7-Amino-3-[(1'R,2'S,3'R)-4'-hydroxymethyl-2',3'-dihydroxy-4'-cyclopenten-1'-yl]-3H-1,2,3-triazolo[4,5-d]pyrimidine (Formula 25) (8-Azaneplanocin A)

The protected 8-azaneplanocin A (19) (39 mg, 0.1 mmol) was dissolved in 3 mL of CH$_2$Cl$_2$ and the resulting solution was cooled to −76° C. Boron trichloride (0.8 mL of a 1M solution in CH$_2$Cl$_2$, 0.8 mmol) was added. The reaction was stirred at −76° C. for 2 h and then allowed to warm to 0° C. before being quenched by the addition of methanol. Removal of the solvents in vacuo followed by the addition and evaporation of a further 40 mL of methanol from the reaction mixture gave a yellow oil. The oil was dissolved in a minimum of ethanol and diluted ten-fold with ethyl acetate to give 10 mg of 25 (38%) as an off-white powder; mp 9295° C. (dec); $^1$H-NMR (CD$_3$OD) δ 4.37 (s, 2H, H-6'$_{a,b}$), 4.64 (t, J=5.8 Hz, 1H, H-2'), 4.73 (d, J=5.8 Hz, 1H, H-3'), 5.95 (m, 2H, H-1' and H-5'), 8.48 (s, 1H, H-2); MS (FAB) m/e 265 (HM+), 137 (base+2H).

EXAMPLE X

1-[(1'R,2'S,3'R)-4'-hydroxymethyl-4'-cyclopenten-1'-yl]-2(1H)-pyrimidinone (Formula 26) (CPE-U)

A solution of 6 (1.02 g, 2.78 mmol) in dry dichloromethane (50 mL) was chilled to −78° C. and treated with boron trichloride [10 mL (3.7 equiv.) of a 1M solution in dichloromethane] and stirred at that temperature for 3 h. The solution was warmed up to 24° C., and quenched with methanol (50 ml) and reduced to dryness. This operation was repeated three times. Purification of the residue by flash chromatography (CH$_2$Cl$_2$:MeOH, 4:1) gave 205 mg (31%) of pure 26 as a white foam; [α]$_D^{24}$ −62° (c 0.47, H$_2$O); UV (H$_2$O) λ$_{max}$ 266 nm (log ε 4.07); $^1$H-NMR (D$_2$O) δ 4.18 (m, 1H, H-2'), 4.32 (br s, 2H, H-6'$_{a,b}$), 4.62 (d, J=5.5 Hz, 1H, H-3'), 5.52 (m, 1H, H-1'), 5.82 (m, 1H, H-5'), 5.90 (d, J=8.0 Hz, 1H, H-5), 7.52 (d, J=8.0 Hz, 1H, H-6); MS (FAB) m/e 241 (MH+).

Biological Activity

The effect of 3-deazaneplanocin A (also called C$^3$ neplanocin) on hamster liver adenosine-homocystine (AdoHyc) hydrolase was studied. The results (FIG. 1) show that the compound behaves as a competitive inhibitor of the enzyme with adenosine, with a K$_i$=5×10$^{-11}$M. This result indicates that this inhibitor is 250-fold more potent than the most potent inhibitor of this enzyme previously known, 3-deazaaristeromycin.

Figure 2:
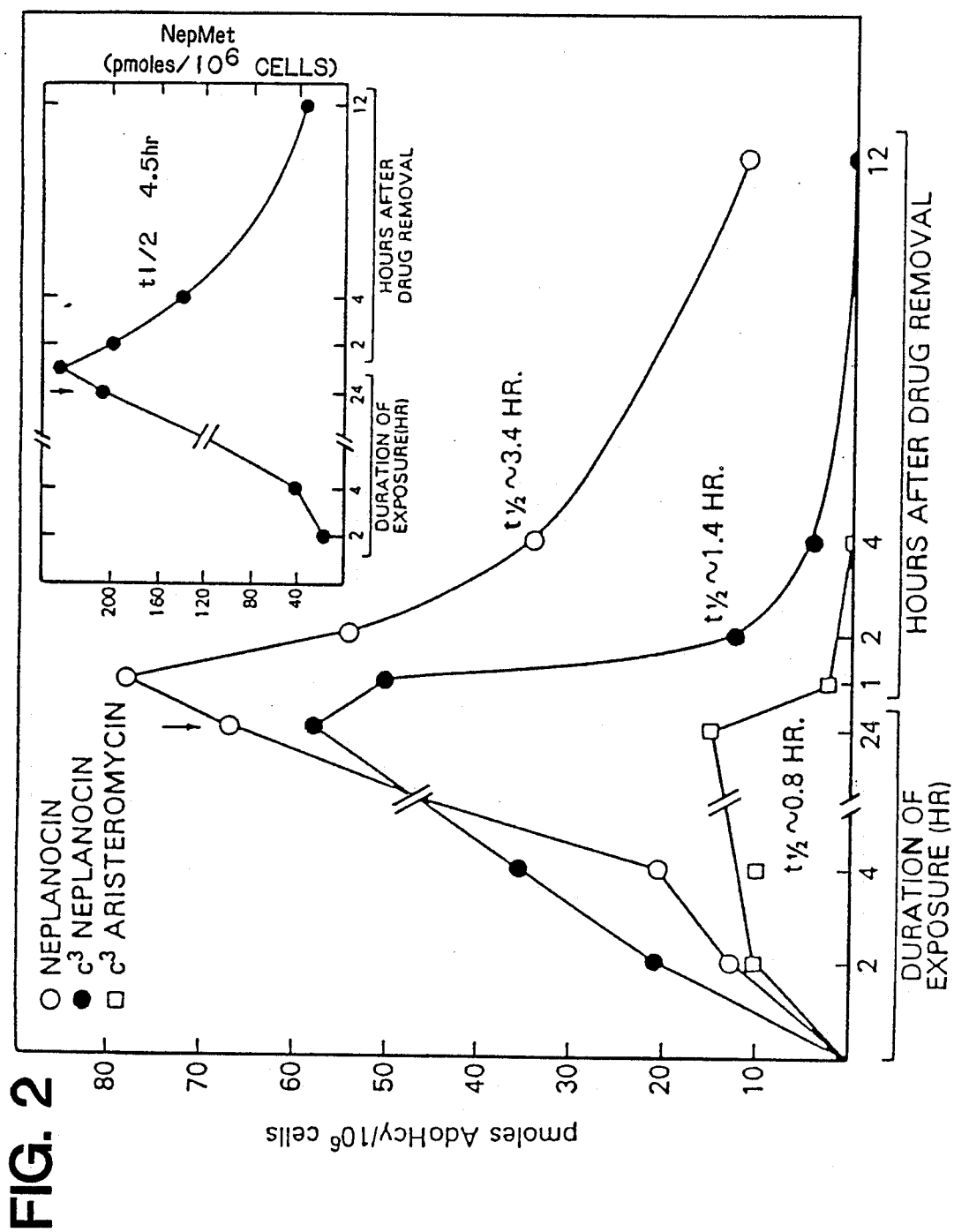
FIG. 2 shows AdoHcy levels in HL-60 cells treated with 3-deazaneplanocin A, 3-deazaaristeromycin or neplanocin A. The cells were treated with 3-deazaneplanocin A ($10^{-5}$M), 3-deazaaristeromycin ($10^{-5}$M) or neplanocin A ($10^{-6}$M). AdoHcy concentrations were determined by HPLC analysis. The inset shows the formation and disappearance of neplanocylmephionine (NepMet). Each value is the mean of at least 2 determinations.

To obtain a measure of the effectiveness in vitro of 3-deazaneplanocin A as an inhibitor of AdoHcy hydrolase, HL-60 cells were exposed for 24 hrs. to this drug as well as the closely related analogs, neplanocin A and 3-deazaaristeromycin (FIG. 2). AdoHyc accumulated rapidly after exposure to 3-deazaneplanocin A and reached a peak after 24 hrs. of drug exposure. The levels of AdoHcy were 4-fold greater after treatment with 10$^{-5}$M 3-deazaneplanocin A than after exposure to an equimolar concentration of 3-deazaaristeromycin. Neplanocin A at 10$^{-6}$M also produced an equivalent accumulation of AdoHcy, as well as an even greater amount of the anabolite, neplanocylmethionine, which is not formed from the other two analogs (FIG. 2 and inset). The half-life for the disappearance of AdoHcy following drug removal was twice as great for 3-deazaneplanocin a vs 3-deazaaristeromycin, but considerably shorter than after removal of neplanocin A. The advantage of 3-deazaneplanocin A over neplanocin A is its low degree of acute cytotoxicity to HL-60 cells. Little or no change in cell viability occurred following two days of continuous 3-deazaneplanocin exposure, whereas neplanocin A is more toxic to this cell line after 24 hrs. of drug exposure at an equimolar concentration. This reduced toxicity provides excellent selectivity and potency as an antiviral agent.

Figure 3:
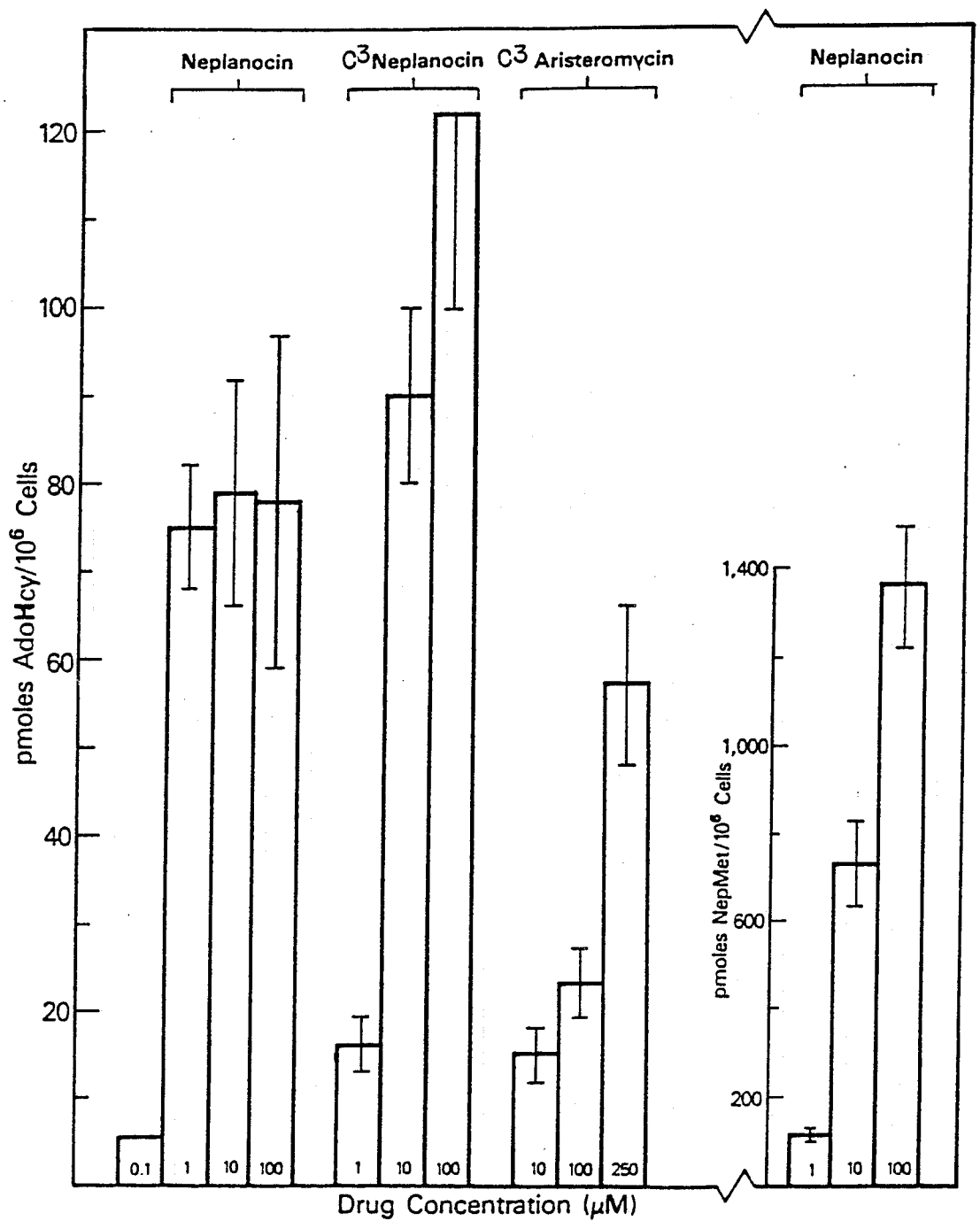
FIG. 3 shows AdoHcy levels in HT-29 cells treated for 24 hours with neplanocin A, 3-deazaneplanocin A (C3-neplanocin A) and 3-deazaaristeromycin A (C3 aristeromycin). On the right is shown the level of Nep Met produced by neplanocin A treatment. Each value is the mean ISE of 6–8 experiments.

Inhibitory activity against AdoHcy-ase in vitro was also ascertained in intact HT-29 cells by measuring the elevation in AdoHcy concentration in cell extracts (FIG. 3). Neplanocin A produced an increase in AdoHcy beginning at 0.1 μM drug and elevated AdoHcy concentration to 80 pmoles/10$^6$ cells at 1 to 100M drug. The elevation of the methionine metabolite (NepMet) which correlates with the cytotoxicity of neplanocin A was also observed. 3-Deazaneplanocin A and 3-deazaaristeromycin did not form a similar metabolite. 3-Deazaneplanocin at 100 μM elevated AdoHcy levels to 120 pmoles/10$^6$ cells which was 6-fold higher than that produced by 3-deazaaristeromycin at this concentration.

To ascertain if elevations of AdoHcy correlated with antiviral activity, 3-deazaneplanocin A was evaluated against three RNA viruses: Dengue type II, Polio type III, and Coxsackie A9.. At noncytotoxic concentrations, potent activity was observed against all three viruses (Table 1).

Antiviral activity was also observed for CPE-C (Formula 22). This compound had excellent activity against the DNA viruses Herpes Simplex Type II and Adenovirus Type 7, at non-cytotoxic concentrations (Table 2). CPE-U (Formula 26) was less effective as a general antiviral agent but showed good activity against the Dengue Type II RNA virus (Table 3).

CPE-C (Formula 22) was also a potent cancer cell differentiating agent. The effect of this compound on differentiation, and nucleic acid and nucleotide biosynthesis were examined in the malignant human promyelocytic leukemia cell line, HL-60. Continuous exposure for 5 days to 10$^{-8}$ to 10$^{-6}$M concentrations produced progressive inhibition of cell growth as well as differentiation to a non-malignant phenotype as measured by nitroblue tetrazolium reduction. During this exposure interval, pronounced differentiation to mature myeloid cells occurred wherein 95% of the cell population reduced nitroblue tetrazolium four days after exposure to 10$^{-7}$M CPE-C. Preceding differentiation was the inhibition of DNA synthesis which was only 10% of control levels 24 hrs. after exposure to 10$^{-7}$M CPE-C, while RNA synthesis was inhibited to a lesser extent. The induction of mature myeloid cells by CPE-C was preceded by the inhibition of c-myc mRNA levels which was more pronounced than the reduction in total cellular RNA synthesis. During the interval of CPE-C treatment, there was a rapid and pronounced inhibition in the level of CTP, but not of UTP, ATP or GTP, where the half-life for the disappearance of CTP was 1.5 to 2 hrs. Following drug removal, cells treated with CPE-C showed a sustained reduction in CTP levels. These results indicated that the reduction in CTP levels leads to rapid inhibition of DNA synthesis and reduction in c-myc levels which precede the appearance of non-malignant, differentiated HL-60 cells. 8-Aza-CPE-A (Formula 25) displayed significant cytotoxicity against L1210 tumor cells in culture with an IC$_{50}$ of 3 μM measured after a 48 hour exposure.

TABLE 1

| | Antiviral Effect of 3-Deazaneplanocin (Formula 9) | | |
|---|---|---|---|
| | RNA Virus Type | | |
| Concentration[a] (μg/ml) | Dengue II[b] (% PFU Reduction)[e] | Polio III[c] (% PFU Reduction) | Coxsackie 9A[d] (% PFU Reduction) |
| 50 | 98.9 | 83.3 | 89.4 |
| 25 | 95.0 | 77.7 | 77.2 |
| 5 | 14.2 | 44.4 | 69.4 |

[a]Concentrations listed were non-toxic to cells used to support virus growth.
[b]Dengue virus Type II, strain 16681 in Vero E6 cells. Multiplicity of infection (MOI) 0.1 PFU/ml.
[c]Polio Type III virus Sabin oral polio vaccine strains, passage PMK3 in Viro E6 cells. MOI 0.1 PFU/ml.
[d]Coxsackie A9 virus, strain 1861, passive V.10, PMK3 in Viro E6 cells. MOI 0.1 PFU/ml.
[e]Plaque forming units (PFU) is a meausre of the infectivity of the virus.

TABLE 2

| | Antiviral Effect of CPE-C (Formula 22) | | | |
|---|---|---|---|---|
| | DNA Viruses | | RNA Viruses | |
| Concentration[a] (μg/ml) | Herpes Simplex II[b] (% PFU Reduction)[d] | Adenovirus 7[c] (% PFU Reduction) | Polio Type III[g] (% PFU Reduction) | Dengue Type II[h] (% PFU Reduction) |
| 50 | 97.4 | 100 | 94.6 | 95 |
| 25 | 95.7 | 99.5 | 82.1 | 2.5 |
| 5 | 98.7 | 98.6 | 73.2 | 0.0 |

Note: Adenovirus 7 values: 94, 80, 70.

[a] Concentrations listed were non-cytotoxic to cells used to support virus growth.
[b] Herpes Simplex Type II virus, strain 28382 in mink lung cells.
[c] Adenovirus Type 7, strain V1-012 in Hep-2 cells.
[d] Plaque forming units (PFU) is a measure of the infectivity of the virus.
[e] Multiplicity of infection (MOI) 2.0 PFU/ml.
[f] MOI 0.2 PFU/ml.
[g] Polio virus Type III (sabin oral vaccine strain), passage PMK3 in Viro E6 cells.
[h] Dengue virus Type II, strain 16681, passage LLCMK2-1-C636-P4 in BHK21 cells

TABLE 3

| | Antiviral Effect of CPE-U (Formula 26) |
|---|---|
| Concentration[a] (μg/ml) | RNA Virus Dengue Type II[b] (% PFU Reduction)[c] |
| 50 | 93 |
| 25 | 91 |
| 5 | 2 |

[a] Concentrations listed were non-cytotoxic to cells used to support virus growth.
[b] Dengue virus Type II, strain 16681, passage LLCMK2-1-C636-P4 in BHK21 cells.
[c] Plaque forming units (PFU) is a measure of the infectivity of the virus.

What is claimed is:

1. 3-Deazaneplanocin A.

2. A method of treating viral diseases wherein the viruses causing said viral diseases require a methylated 5'-cap structure on their m-RNA comprising administering an effective amount of 3-deazaneplanocin A.

3. A pharmaceutical composition for treating viral diseases comprising the compound of claim 1 and a pharmaceutically acceptable carrier.

4. A compound of the formula:

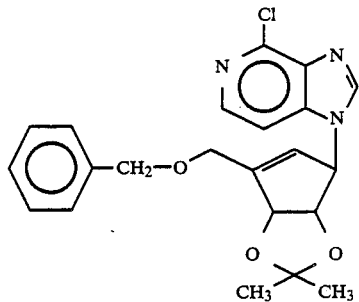

or

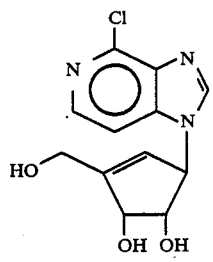

* * * * *